United States Patent
Wu et al.

(10) Patent No.: US 6,407,292 B1
(45) Date of Patent: Jun. 18, 2002

(54) PREPARATION OF ALKYLATED DIPHENYL OXIDES

(75) Inventors: Margaret M. Wu, Skillman; Rene B. Lapierre, Medford, both of NJ (US); Gilbert R. Jersey, West Chester, PA (US); Andrew Gene Horodysky, Cherry Hill, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/474,354

(22) Filed: Dec. 29, 1999

Related U.S. Application Data

(60) Provisional application No. 60/114,245, filed on Dec. 30, 1998.

(51) Int. Cl.$^7$ ............................................. C07C 41/05
(52) U.S. Cl. ........................................ 568/628; 568/635
(58) Field of Search .................................. 568/628, 635, 568/58; 544/35

(56) References Cited

U.S. PATENT DOCUMENTS

| | | | |
|---|---|---|---|
| 4,891,448 A | 1/1990 | Garces et al. | 568/628 |
| 5,004,841 A | 4/1991 | Lee et al. | 568/678 |
| 5,552,071 A | 9/1996 | Rudnick et al. | 508/581 |
| 5,955,404 A | * 9/1999 | Horodysky et al. | 508/294 |

* cited by examiner

*Primary Examiner*—Rosalynd Keys
(74) *Attorney, Agent, or Firm*—Louis N. Moreno

(57) ABSTRACT

A continuous process for the manufacture of alkylated diphenyl compounds such as diphenyl ether and diphenyl sulfides by alkylating a diphenyl compound such as diphenyl ether with an olefinic alkylating agent by passing a continuous flow of the diphenyl compound and the olefin over a solid particulate catalyst which comprises a molecular sieve of the MCM-22 family. The process is flexible. By adjusting feed compositions, products of different compositions and wide range of properties are produced.

10 Claims, No Drawings

PREPARATION OF ALKYLATED DIPHENYL OXIDES

CROSS REFERENCE TO RELATED APPLICATIONS

This application claims priority of U.S. Provisional Patent Application Ser. No. 60/114,245, filed Dec. 30, 1998.

FIELD OF THE INVENTION

This invention relates to a method for the manufacture of alkylated diphenyl oxides in a convenient continuous flow process.

BACKGROUND OF THE INVENTION

Alkylated diphenyl oxide (ADPO) can be used as high performance synthetic base stocks or as starting material for high performance detergents. Polyphenyl ethers are known for their high temperature properties as noted in *"Lubricants end Related Products"*, Klamann, Verlag Chemie, 1984, pp. 116–121. These products can be used as high performance lubricant base stocks or can be used as starting material for high performance detergents such as the sulfonated ADPO which has been reported as a class of high performance detergent. The known commercial methods for preparing ADPO use Friedel-Crafts catalysts which are not only hazardous but also expensive, being consumed at stoichiometric rates in the reaction but also require aqueous workup; the large amounts of catalyst residues also present disposal problems. The use of zeolites such as ultra-stable Y catalysts has been proposed, for example, in U.S. Pat. No. 5,552,071 (Rudnick) where zeolites such as USY and MCM-22 are proposed for batch operation. Batch processes are not, however, suitable for large-scale and continuous production. The USY catalyst as disclosed in U.S. Pat. No. 5,552,071 deactivates quickly and large amount of catalyst is needed to achieve high conversion. This solid catalyst is usually not easily regenerable when used in this type of process and, as a result, has to be disposed as solid waste. There is therefore a need for a continuous process for the production of ADPOs using solid catalyst with long cycle durations in a continuous, fixed bed reactor.

SUMMARY OF THE INVENTION

We have now found that the catalysts belong to MCM-22 family of molecular sieves have superior activity and can be used in continuous processes to produce ADPO economically in large scale without generating large volumes of catalyst waste.

According to the present invention we therefore provide a continuous process for the manufacture of ADPO by alkylating a diphenyl compound such as diphenyl ether itself with an olefinic alkylating agent by passing a continuous flow of the ether and the olefin under alkylation conditions over a solid particulate catalyst which comprises a molecular sieve of the MCM-22 family, preferably zeolite MCM-22. The process is flexible. By adjusting feed compositions, ADPO of different compositions and wide range of properties are produced.

DETAILED DESCRIPTION

The diphenyl ether reactant is reacted with the olefinic alkylating agent in the presence of the solid molecular sieve catalyst in a continuous flow process in which the catalyst is held in a fixed bed with the reactants being passed over it under fluid flow conditions. The reactants may be in the liquid, gas or mixed (liquid/gas) phases with liquid phase operation being preferred. The temperatures for the reaction will typically be at least ambient and normally will range up to about 400° C. although 200° C. (reactor inlet) represents a useful practical working maximum. Pressure may range from ambient up to any range within the equipment rating although in most cases autogenous pressure may be suitable. Typically pressures will range up to no more than about 3,000 kPa (reactor inlet) to permit the use of conventional low pressure equipment. Space velocity (WHSV) will typically be from about 0.1 to 10, more usually from about 0.2 to 2.0 $hr^{-1}$. The catalyst is maintained in a fixed bed and for this purpose, the catalyst is formulated in the conventional manner into particulate form with a size suitable to maintain an acceptable pressure drop across the fixed bed. The molecular sieve component may be formulated into the finished particulate catalyst with binders or matrix materials such as alumina, silica or silica-alumina as is conventional or may be a self-bound catalyst. Particles may be cylindrical, lobed, hollow cylindrical, or other suitable configurations for maintaining bed pressure drop within limits.

The aromatic compound which is alkylated is a diphenyl ether or sulfide compound, that is a compound containing at least two aromatic rings linked by an oxygen or sulfur bridge. This class of compounds includes diphenyl ether itself, which is a preferred starting material both from the view point of cost as well as from the properties of the final products as well as diphenyl sulfide. It also includes the substituted diphenyl ethers where the substituents may typically be hydrocarbon substituents such as alkyl, aryl, alkaryl, or aralkyl groups but other substituents such as phenolic hydroxyl, mercapto, halo may also be present. The bridging atoms need not be limited to oxygen or sulfur as in the diphenyl oxides and sulfides and phenoxathins but may also include nitrogen as in the phenothiazines.

The alkylating agent is an olefinic alkylating agent, normally a hydrocarbon olefin although substituted olefins may also be used. For superior lubricating properties, the longer chain alkyl groups are preferred in the final product, typically from at least eight carbon atoms and preferably at least 10 carbon atoms in order to confer good lubricating performance and good oil solubility characteristics in paraffinic type lubricant materials. For this purpose, olefins of at least eight carbons are preferred although less than eight carbons such as hexene-1 may be used in a similar way. Olefins such as octene, decene, dodecene, tetradecene, hexadecene and octadecene are therefore preferred since olefins of more than 18 carbon atoms do not confer improved solubility or lubricant performance characteristics while tending to cause a deterioration in low temperature viscometrics. The alpha olefins, conveniently available commercially, typically from the ethylene growth reaction, are preferred since they produce alkyl substituents on the aromatic rings which are linear beyond the point of ring attachment and with only a methyl branch at the point of attachment. Thus, the preferred olefinic alkylating agents for alkylated diphenyl ethers which are to be used as lubricants are octene-1, decene-1, dodecene-1, tetradecene-1, hexadecene-1 and octadecene-1. Longer chain olefins such as the long chain olefins sold commercially as "Gulftene" (™) may be used if desired, for example, for the manufacture of intermediates where a long alkyl chain is required.

The ratio between the diphenyl ether and the alkylating agent is typically from 1:10 to 10:1 molar although considerable excesses of either reactant may be tolerated, especially of the olefin. Normally, ratios between 1:5 and 5:1 molar are useful. Depending on the ratio, the degree of alkylation may be varied although for lubricant purposes, monoalkylation has been found to provide superior results, as described in U.S. Pat. No. 5,552,071. Ratios between 1:2 and 2:1 molar will be most commonly used.

The alkylation reaction is carried out in the presence of a particulate catalyst which comprises a molecular sieve of the MCM-22 family, preferably zeolite MCM-22. The MCM-22 family comprises the molecular sieve materials MCM-22, MCM-56 and MCM-49. MCM-22 is described in U.S. Pat. Nos. 4,954,325 and 5,100,534 and 5,103,066; MCM-49 and MCM-56 are described in U.S. Pat. Nos. 5,362,697; 5,453,554; 5,557,024; 5,827,491; 5,362,697 and 5,536,894, to which reference is made for a description of these molecular sieves, their properties and methods for their manufacture.

The MCM-22 family catalyst is a solid, long-lasting, highly productive and regenerable catalyst for producing ADPO class compounds. These type of catalysts has much higher productivity and longer catalyst life time than previous reported USY or other zeolites. They are highly suitable for use in the fixed-bed, continuous operation characteristic of the present manufacturing process.

EXAMPLE 1

Two grams of a self-bound MCM-22 catalyst crushed and sized to 24/60 mesh size from 3 mm extrudate was loaded into a continuous fixed bed reactor of 12 mm inside-diameter. The catalyst was purged with nitrogen at 200° C. for 16 hours. A mixture of 42.9% diphenyl oxide and 57.1% 1-hexadecene of 1/1 molar ratio was fed through the reactor (Table 1). After adjustment of reaction conditions, reactor temperature was set at 175° C. and total liquid feed rate at 4 gram/hour. After a brief line-out time (LO5 run in Table 1), the catalyst activity remained constant for 180 hours (run MB5 to MB13). The reaction was terminated while the catalyst was still fully active. During this time, the conversion for the total feed was 83%, for 1-hexadecene 96% and diphenyl oxide 66%. Selectivity to alkylated diphenyl oxide was >95%. The results are shown in Table 1 below.

TABLE 1

ADPO from DPO and 1-C16 (1/1 molar), MCM-22

| Run no | MB1* | MB2 | MB3 | MB4 | LO5 | MB5 | MB6 |
|---|---|---|---|---|---|---|---|
| Duration, hrs. | 1 | 2 | 15.5 | 8 | 16.5 | 6.5 | 17 |
| Temp. C. | 150 | 150 | 150 | 150 | 175 | 175 | 175 |
| WHSV, g/g/hr | 11 | 11 | 2 | 2 | 2 | 2 | 2 |
| Material balance | 89 | 96 | 88 | 102 | 98 | 100 | 95 |
| Product composition by gc, wt % | | | | | | | |
| Light ends | 0.0 | 0.9 | 0.4 | 0.2 | 0.2 | 0.1 | 0.2 |
| DPO | 23.6 | 36.4 | 26.6 | 26.6 | 19.3 | 16.0 | 14.9 |
| C16= | 52.8 | 45.2 | 28.3 | 29.5 | 12.1 | 4.6 | 2.8 |
| MADPO | 15.3 | 16.4 | 39.5 | 40.0 | 56.4 | 61.9 | 61.0 |
| DADPO | 8.3 | 1.2 | 5.1 | 3.7 | 11.4 | 16.3 | 19.3 |
| Others | 0.0 | 0.0 | 0.0 | 0.0 | 0.6 | 0.5 | 1.0 |
| % Conv. | 24 | 18 | 45 | 44 | 68 | 79 | 82 |
| % DPO Conv. | 52 | 19 | 40 | 40 | 57 | 64 | 66 |
| % C16 Conv. | 20 | 24 | 52 | 50 | 79 | 92 | 95 |
| % ADPO Select. | 87 | 96 | 97 | 97 | 97 | 96 | 96 |
| % Mono-ADPO | 65 | 93 | 89 | 91 | 83 | 79 | 76 |
| % Di-ADPO | 35 | 7 | 11 | 9 | 17 | 21 | 24 |
| Others | 0 | 0 | 0 | 0 | 1 | 1 | 1 |

| Run no | MB7 | MB8 | MB9 | MB10 | MB11 | MB12 | MB13 |
|---|---|---|---|---|---|---|---|
| Duration, hrs. | 6.5 | 17 | 23 | 25.25 | 24 | 24.5 | 19.75 |
| Temp., C. | 175 | 175 | 175 | 175 | 175 | 175 | 175 |
| WHSV, g/g/hr | 2 | 2 | 2 | 2 | 2 | 2 | 2 |
| Material balance | 99 | 94 | 96 | 98 | 97 | 97 | 96 |
| Product composition by gc, wt % | | | | | | | |
| light end | 0.1 | 0.4 | 0.1 | 0.2 | 0.1 | 0.1 | 0.0 |
| DPO | 15.0 | 15.4 | 15.5 | 14.9 | 14.9 | 14.9 | 13.3 |
| C16= | 2.7 | 2.8 | 2.7 | 2.9 | 2.9 | 2.6 | 1.8 |
| MADPO | 62.4 | 60.9 | 61.0 | 60.8 | 61.1 | 61.5 | 58.5 |
| DADPO | 18.8 | 19.9 | 19.5 | 19.6 | 19.2 | 19.6 | 23.8 |
| Others | 1.0 | 0.0 | 0.6 | 0.9 | 1.0 | 0.7 | 2.0 |
| % Total Conv. | 82 | 81 | 82 | 82 | 82 | 82 | 85 |
| % DPO Conv. | 66 | 65 | 65 | 67 | 67 | 67 | 70 |
| % C16 Conv. | 96 | 95 | 96 | 95 | 95 | 96 | 97 |
| % ADPO Select. | 97 | 96 | 95 | 95 | 95 | 96 | 97 |
| % mono-ADPO | 77 | 75 | 76 | 76 | 76 | 76 | 71 |
| % Di-ADPO | 23 | 25 | 24 | 24 | 24 | 24 | 28 |
| Others | 1 | 0 | 1 | 1 | 1 | 1 | 2 |

MADPO - mono-alkylated diphenyl oxide
DADPO - di-alkylated diphenyl oxide

EXAMPLE 2

This was carried out a similar manner to Example 1, except a USY catalyst (Englehard) was charged into the fixed bed reactor (Table 2). As these data demonstrated that the total conversion by the USY catalyst was never higher than 10%.

These two examples clearly demonstrate that MCM-22 is a much preferred catalyst than USY for ADPO production.

TABLE 2

ADPO from DPO and 1-C16 (1/1 molar), USY

| Run no | Starting mixture | MB1 | MB2 | MB3 | LO4 | MB4 |
|---|---|---|---|---|---|---|
| Duration, hrs. | | 22 | 25 | 24 | 24 | 24 |
| Temperature, C. | | 175 | 175 | 175 | 200 | 200 |
| WHSV, g/g/hr | | 1 | 1 | 1 | | 1 |
| Material balance | | 89 | 97 | 97 | | 96 |
| Product composition by gc, wt % | | | | | | |
| Light ends | 0 | 0.409 | 0.426 | 0.542 | 0.431 | 0.497 |
| DPO | 42.9 | 39.505 | 41.383 | 41.638 | 41.703 | 41.549 |
| C16= | 57.1 | 53.248 | 57.498 | 57.863 | 57.334 | 56.291 |
| Unknown | | 0.257 | 0.119 | 0.077 | 0.113 | 0.159 |
| MADPO | | 6.753 | 0.944 | 0.376 | 0.796 | 1.943 |
| DADPO | | 0.176 | 0 | 0 | 0 | 0.002 |
| % Total Conversion | | 7 | 1 | 0 | 1 | 2 |
| % ADPO Selectivity | | 96 | 84 | 75 | 83 | 90 |
| % mono-ADPO | | 97 | 100 | 100 | 100 | 100 |
| % di-ADPO | | 3 | 0 | 0 | 0 | 0 |
| % Uknown 1 Selectivity | | 4 | 11 | 15 | 12 | 7 |

(*) - gc wt % were calculated by sim-dist. method
MADPO - mono-alkylated diphenyl oxide
DADPO - di-alkylated diphenyl oxide

EXAMPLE 3

In a flask, 90 gram 1-hexadecene and 82 gram DPO (molar ratio of DPO/1-C16 was 1.2) were mixed and heated to 200° C. under nitrogen atmosphere. 1.72 gram of a MCM-22 catalyst (crushed powder of the self-bound catalyst, 1 wt % of total feed) was added. Samples were taken after two hours and analyzed on gc (Table 3). The data showed that the reaction was complete after 4 hours of reaction time.

TABLE 3

ADPO from DPO and 1-C16 (1.2/1 molar), MCM-22, 200° C.

| Run no | Feed | 1 | 2 | 3 | 4 | distilled Pdt |
|---|---|---|---|---|---|---|
| Time, hrs. | 0 | 2 | 4 | 6 | 7.5 | |
| Product composition by gc, wt % | | | | | | |
| Light ends | 0.0 | 0.1 | 0.1 | 0.1 | 0.1 | 0.1 |
| DPO | 45.6 | 22.0 | 18.6 | 18.3 | 18.2 | 0.0 |
| C16= | 54.2 | 6.4 | 2.8 | 2.3 | 2.4 | 0.0 |
| MADPO | 0.0 | 58.4 | 62.2 | 60.8 | 60.6 | 76.8 |
| Unknown | 0.0 | 0.5 | 0.0 | 0.7 | 0.7 | 0.0 |
| DADPO | 0.0 | 12.4 | 14.8 | 16.5 | 16.9 | 21.9 |
| Others | 0.2 | 0.2 | 1.2 | 1.3 | 1.3 | 1.3 |
| | 100.0 | 100.0 | 100.0 | 100.0 | 100.0 | 100.2 |
| % Total Conv. | 0 | 72 | 79 | 79 | 79 | 79 |
| % DPO Conv. | | 52 | 59 | 60 | 60 | 100 |
| % C16 Conv. | | 88 | 95 | 96 | 96 | 100 |
| % ADPO Select. | 0 | 99 | 98 | 97 | 97 | 97 |
| % mono-ADPO | 0 | 82 | 81 | 79 | 79 | 78 |
| % Di-ADPO | 0 | 18 | 19 | 21 | 21 | 22 |

EXAMPLE 4

This was carried out similarly to Example 3, except 100 gram 1-hexadecene and 152 gram DPO (molar ratio of DPO/1-C16 was 2) and 1.26 gram of MCM-22 catalyst (0.5 wt %) were charged into the reactor. The results (Table 4) showed that the reaction was complete after 6 hours of reaction. This example also demonstrated that the product properties and the composition of ADPO can be controlled by adjusting feed composition.

TABLE 4

ADPO from DPO and 1-C16 (2.0/1 molar ratio), MCM-22, 200° C.

| Run No. | Feed | 1 | 2 | 3 | 4 | Final Pdt |
|---|---|---|---|---|---|---|
| Time, hrs | | 2 | 4 | 6 | 7.5 | |
| Product comn by gc, wt % | | | | | | |
| Light ends | 0 | 0.008 | 0.013 | 0.01 | 0.02 | 0 |
| DPO | 60.3 | 41.921 | 34.639 | 34.094 | 34.451 | 0.655 |
| C16= | 39.7 | 9.58 | 2.356 | 1.742 | 1.355 | 0 |
| Unknown | 0 | 0.046 | 0.584 | 0 | 0 | 0 |
| MADPO | 0 | 44.888 | 54.813 | 55.548 | 55.429 | 85.841 |
| DADPO | 0 | 3.497 | 7.505 | 8.526 | 8.659 | 13.382 |
| Others | 0 | 0.06 | 0.06 | 0.081 | 0.086 | 0.122 |
| % Total Conv. | 0 | 48 | 63 | 64 | 64 | 99 |
| % DPO Conv. | | 30 | 43 | 43 | 43 | 99 |
| % C16 Conv. | | 76 | 94 | 96 | 97 | 100 |
| % ADPO Select. | | 100 | 99 | 100 | 100 | 100 |
| % mono-ADPO | | 93 | 88 | 87 | 86 | 87 |
| % Di-ADPO | | 7 | 12 | 13 | 14 | 13 |

EXAMPLE 5

Under the similar reaction conditions of Example 4, 3–5 wt % of USY catalyst was needed to achieve >80% conversion within 8 hours of reaction time.

The product properties of Example 1 to 4 together with USY products are summarized in Table 5 below.

TABLE 5

ADPO Product Properties

|  | Example 1 | Example 3 | Example 4 | Example 5 |
|---|---|---|---|---|
| Catalyst | MCM-22 | MCM-22 | MCM-22 | USY |
| Molar ratio of DPO/C16 | 1.0 | 1.2 | 2.0 | 1.0 |
| Temp, C. | 175 | 175 | 200 | 200 |
|  | Fixed bed run | batch | batch | batch |
| wt % catalyst charge | — | 1 | 0.5 | 3–5 |
| % Total conv. | 76 | 79 | 64 | 80 |
| % 1-C16 conv. | 96 | 96 | 97 | — |
| % DPO conv. | 67 | 60 | 43 | — |
| % Mono-ADPO | 76 | 79 | 86 | 97 |
| % Di-ADPO | 24 | 21 | 14 | 3 |
| % Di-ADPO after distillation | 32 | 22 | 13 | 3 |
| Lube properties |  |  |  |  |
| V 100° C., cS | 6.0 | 5.55 | 4.86 | 4.44 |
| V 40 C., cS | 36.27 | 34.16 | 27.14 | 23.62 |
| VI | 109 | 98 | 100 | 96 |
| Pour point, C. | −41 | −50 | −40 | −50 |

We claim:

1. A continuous process for the manufacture of alkylated diphenyl compounds by alkylating a diphenyl compound with an olefinic alkylating agent by passing a continuous flow of the diphenyl compound and the olefin over a solid particulate catalyst which comprises a molecular sieve of the MCM-22 family under alkylation conditions.

2. A process according to claim 1 in which the diphenyl compound comprises diphenyl ether.

3. A process according to claim 1 in which the alkylating agent comprises an olefin of 8 to 18 carbon atoms.

4. A process according to claim 3 in which the olefin comprises an alpha olefin of 8 to 18 carbon atoms.

5. A process according to claim 1 in which the molecular sieve comprises zeolite MCM-22.

6. A process according to claim 1 in which the reaction is carried out at a temperature from ambient to 200° C.

7. A process according to claim 1 in which the reaction is carried out under a pressure from ambient to 3,000 kPa.

8. A process according to claim 1 in which the molar ratio of the diphenyl compound to the alkylating agent is from 1:2 to 2:1.

9. A process according to claim 1 in which the diphenyl compound comprises diphenyl ether and the olefinic alkylating agent comprises a $C_{10}$ to $C_{14}$ 1-olefin.

10. A process according to claim 9 in which the 1-olefin comprises 1-tetradecene or 1-hexadecene.

* * * * *